(12) United States Patent
Periasamy et al.

(10) Patent No.: US 8,679,460 B2
(45) Date of Patent: Mar. 25, 2014

(54) LOW OSMOLAR X-RAY CONTRAST MEDIA FORMULATIONS

(75) Inventors: Muthunadar P. Periasamy, Chesterfield, MO (US); Brian D. Doty, St. Peters, MO (US)

(73) Assignee: Mallinckrodt LLC, St. Louis, MO (US)

( * ) Notice: Subject to any disclaimer, the term of this patent is extended or adjusted under 35 U.S.C. 154(b) by 1321 days.

(21) Appl. No.: 10/588,674

(22) PCT Filed: Mar. 11, 2005

(86) PCT No.: PCT/US2005/008389
§ 371 (c)(1),
(2), (4) Date: Aug. 8, 2006

(87) PCT Pub. No.: WO2005/087272
PCT Pub. Date: Sep. 22, 2005

(65) Prior Publication Data
US 2008/0317675 A1    Dec. 25, 2008

Related U.S. Application Data

(60) Provisional application No. 60/552,240, filed on Mar. 11, 2004.

(51) Int. Cl.
*A61K 49/04* (2006.01)
*A61B 5/055* (2006.01)

(52) U.S. Cl.
USPC ......... 424/9.452; 424/9.1; 424/9.37; 424/9.4; 424/9.454

(58) Field of Classification Search
USPC .......... 424/1.11, 9.1, 9.4, 9.42, 9.45; 564/153
See application file for complete search history.

(56) References Cited

U.S. PATENT DOCUMENTS 4,474,747 A    10/1984  Dimo et al.
5,695,742 A *  12/1997  Felder et al. ............... 424/9.455
5,698,739 A *  12/1997  Sovak ........................... 564/153
7,250,153 B2 * 7/2007  Sovak et al. ................ 424/9.452
2010/0135913 A1* 6/2010  Aime et al. .................. 424/9.37

FOREIGN PATENT DOCUMENTS

DE    196 27 309       6/1996
DE    196 27 309       1/1998
WO    WO 93/10825      12/1991
WO    WO 94/14478      12/1992
WO    WO 03/013616     8/2001

OTHER PUBLICATIONS

Dawson, Peter, et al., Textbook of Contrast Media, 1999, pp. 3-14, 35-45, 229-238,297-318,417-427-451-464.
Heinrich, M.C. et al., Cytotoxic effects of ionic high osmolar, nonionic monomeric, and nonionic iso-osmolar dimeric iodinated contrast media on renal tubular cells in vitro, Radiology, Jun. 2005, vol. 235, XP008062300.
Mycek & Pogue, Near-Infrared Imaging with Fluorescent Contrast Agents, Handbook of Biomedical Fluorescence, 2003, Ch. 14, pp. 445-527.
Sovak, M. et al., Iosimenol, a Low-Viscosity Nonionic Dimer, Investigative Radiology, Mar. 2004, vol. 39, No. 3, XP008062184.
Sovak, M., Introduction: State of the Art and Design Principles of Contrast Media, Radiocontrast Agents, Handbook of Experimental Pharmacology, vol. 73, 1984, pp. 1-22.
Swanson, Dennis P. et al., Angiographic Contrast Media, Pharmaceuticals in Medical Imaging, Section I Radiopaque Contrast Media, 1990, pp. 1-77.
Thomsen, H.S. et al., Trends in Contrast Media, 1999, pp. 161-194, 299-309,425-467.
Sovak, Milos, "Contrast Media: A Journey Almost Sentimental," Investigative Radiology, vol. 29, Supplement 1, 1994, pp. S4-S14.

* cited by examiner

*Primary Examiner* — Michael G Hartley
*Assistant Examiner* — Jagadishwar Samala

(57) ABSTRACT

The present invention generally relates to nonionic x-ray contrast media formulations, radiological compositions containing such agents and methods for x-ray visualization utilizing such compositions. The invention especially relates to injectable radiological compositions for x-ray visualization comprising a pharmaceutically acceptable vehicle and a mixture of a monomer, being a triiodo-substituted benzene nucleus, and a dimer, being two linked triiodo-substituted benzene nuclei, such that the mixture demonstrates favorable properties.

29 Claims, No Drawings

LOW OSMOLAR X-RAY CONTRAST MEDIA FORMULATIONS

CROSS-REFERENCE TO RELATED APPLICATIONS

This application is a national stage application of PCT/US2005/008389, filed Mar. 11, 2005, which claims the benefit of U.S. Provisional Application No. 60/552,240, filed March 11, 2004.

BACKGROUND OF THE INVENTION

The present invention generally relates to contrast media formulations and, more particularly, to nonionic x-ray contrast media formulations, radiological compositions containing such formulations and methods for x-ray visualization utilizing such compositions.

The search for ideal contrast media for X-ray radiodiagnostic studies has extended over many decades. Bismuth subnitrate was the first radiocontrast agent used for visualization of the alimentary tract. Later, barium sulfate, a safer agent, was introduced. Barium sulfate has remained the most widely used radiographic agent for the alimentary tract (W. H. Strain, International Encyclopedia of Pharmacology and Therapeutics, Section 76, Vol. 1, Radiocontrast Agents, Chapter 1, Historical Development of Radiocontrast Agents, 1971, Pergamon Press). The inorganic, insoluble oral agents like bismuth subnitrate and barium sulfate serve as valuable tools for gastrointestinal radiodiagnosis.

Unlike gastrointestinal radiodiagnosis, urographic and angiographic X-ray procedures, require intravascular administration of a safe, water-soluble, radiopaque contrast medium. Since the introduction of the water-soluble ionic triiodobenzoic acid derivatives, such as diatrizoic acid and iothalamic acid, in the early 1960's, radiographic visualization of the vascular system has become the most important application of X-ray contrast media. These X-ray procedures are valuable in the diagnosis and evaluation of a variety of diseases that involve or cause alterations in normal vascular anatomy or physiology.

The progress in X-ray contrast media development has been extensively documented; e.g., U. Speck, "X-ray Contrast Media", Medical Division Publication, Department of Medical Information, Schering AG; D. P. Swanson et al., "Pharmaceuticals in Medical Imaging" (1990) McMillan Publishing Co.; M. Sovak, "Radiocontrast Agents", (1984), Springer Verlag. Preferred intravascular X-ray contrast agents possess a combination of desirable properties. Such properties include the following to various degrees: (1) maximum x-ray opacity; (2) biological safety; (3) high water solubility; (4) chemical stability; (5) low osmolality; and (6) low viscosity. In particular, studies have shown that high osmolality can be correlated with undesirable physiologic adverse reactions to x-ray contrast media, e.g., nausea, vomiting, heat and pain.

A significant advancement in the area of triiodobenzene based X-ray contrast media has been the development of non-ionic triiodobenzoic acid derivatives such as iopamidol, iohexyl and ioversol. In general, aqueous solutions of these non-ionic agents have less osmolality than previous agents and hence, provide greater patient comfort when injected. Adverse reactions, especially in the sensation of pain, warmth, and hemodynamic effects are greatly reduced as compared to the ionic triiodobenzoic acid derivatives. However, at equal iodine concentrations, the viscosity values of these non-ionic formulations are higher than for formulations of ionic triiodobenzoic acid based contrast agents.

Further reduction of osmolality of X-ray contrast media resulted from the introduction of non-ionic dimeric agents such as iotrolan and iodixanol. These agents because of isoosmolality values, as compared to the non-ionic monomeric agents, provide even greater patient comfort by reducing nausea and vomiting upon intravenous injection and by causing much less pain upon peripheral arterial injection. However, the frequency and intensity of delayed side reactions in patients are higher for such non-ionic dimers. The viscosity of such non-ionic dimeric agent-based formulations is also substantially greater than for the corresponding monomeric analogs. Thus there remains a need for safe formulations of X-ray contrast media with low viscosity and low osmolality In U.S. Pat. No. 5,698,739 (Sovak), Sovak describes a separate class of dimeric non-ionic X-ray contrast media with at least one primary carboxamide group as a substituent, an example of this class of dimers being Iosmin. According to Sovak, the presence of primary carboxamide group conferred higher iodine content and sterically exposed the hydrophobic character of the neighboring iodine molecules ensuring the formation of aggregates and thus lowering the osmolality.

Another attempt to optimize formulations involves combining a monomer with low viscosity value with a dimer of low osmolality value wherein the substituents on the iodinated aromatic groups are similar. U.S. Pat. No. 5,695,742, discloses injectable aqueous compositions comprising mixtures of non-ionic iodinated aromatic monomers and non-ionic iodinated aromatic dimers having an intermediate osmolality value compared to the pure solutions wherein the mixtures are also disclosed as having a lower viscosity than expected.

With the purpose of decreasing the delayed side reactions seen with the non-ionic dimers, German Patent Application DE 19627309 discloses mixtures comprising monomers and dimers of ionic and non-ionic triiodoaromatic compounds as well as gadolinium complex compounds. Since the mixtures include an ionic contrast agent, the osmolality of such a mixture would be higher than the osmolality value for the pure nonionic dimer contrast agent.

We have now surprisingly discovered novel monomer-dimer mixtures having improved property, e.g. osmolality and viscosity, profiles in which the dimer has at least one primary carboxamide group in the triiodobenzene nuclei and the monomer has no primary carboxamide groups in the triiodobenzene nuclei.

SUMMARY OF THE INVENTION

Among the various aspects of the present invention may be noted the provision of nonionic contrast agents, radiological compositions and methods for x-ray visualization; and the provision of such agents with improved osmolality and viscosity which are substantially non-toxic.

Briefly, the present invention is directed to mixtures comprising at least one monomer and at least one dimer both derived from triiodinated benzene derivatives. The monomer corresponds to Formula I and the dimer corresponds to Formula II;

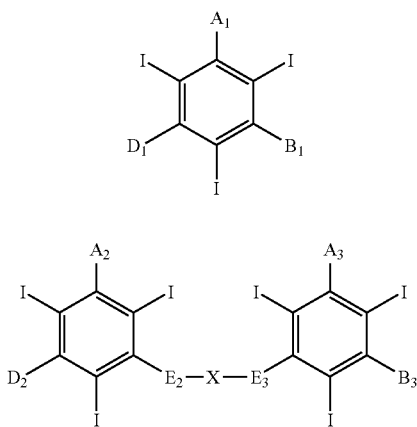

Formula (I)

Formula (II)

wherein

A$_1$, B$_1$, and D$_1$ are independently —CON(R$_3$)R$_1$ or —N(R)C(O)R$_2$;

A$_2$, A$_3$, B$_3$, and D$_2$ are independently —CON(R)R$_1$ or —N(R)C(O)R$_2$ provided, however, at least one of A$_2$ and A$_3$ is —CONH$_2$;

E$_2$ and E$_3$ are independently selected from the group consisting of —CON(R)—, —N(R)C(O)— and —N(COR$_2$)—;

each R is independently H, a linear or branched (C$_1$-C$_8$) alkyl residue optionally substituted with one or more hydroxy, alkoxy or hydroxyalkoxy groups or combinations thereof, or a member of a (C$_3$-C$_7$) cyclic residue, said cyclic residue being optionally interrupted by —O—, —S— or —NR$_4$—, and/or optionally substituted with one or more hydroxy, alkoxy or hydroxyalkoxy groups or combinations thereof, the cyclic residue comprising R, the nitrogen atom to which it is bonded and another moiety, that moiety being (i) —C(O)R$_2$ when A$_1$, A$_2$, A$_3$, B$_1$, B$_3$, D$_1$ or D$_2$ is —N(R)C(O)R$_2$ or (ii) R$_1$ when A$_2$, A$_3$, B$_3$, or D$_2$ is —CON(R)R$_1$;

each R$_1$ is independently (i) hydrogen, (ii) a linear or branched (C$_1$-C$_8$) alkyl residue, optionally substituted with one or more hydroxy, alkoxy, hydroxyalkoxy groups or combinations thereof or by —NRC(O)R$_1$ or —C(O)N(R)R$_1$, (iii) the residue of a carbohydrate, or (iv) a member of a (C$_3$-C$_7$) cyclic residue, said cyclic residue being optionally interrupted by —O—, —S— or —NR$_4$—, and/or optionally substituted with one or more hydroxy, alkoxy or hydroxyalkoxy groups or combinations thereof, the cyclic residue comprising R$_1$, the nitrogen atom to which it is bonded and another moiety, that moiety being (a) R when A$_2$, A$_3$, B$_3$, or D$_2$ is —CON(R)R$_1$ or (ii) R$_3$ when A$_1$, B$_1$, and D$_1$ is —CON(R$_3$)R$_1$;

each R$_2$ is independently (i) a linear or branched (C$_1$-C$_8$) alkyl residue, optionally substituted with one or more hydroxy, alkoxy or hydroxyalkoxy groups, or combinations thereof or (ii) a member of a (C$_3$-C$_7$) cyclic residue, said cyclic residue being optionally interrupted by —O—, —S— or —NR$_4$—, and/or optionally substituted with one or more hydroxy, alkoxy or hydroxyalkoxy groups or combinations thereof, the cyclic residue comprising R$_2$, R, the nitrogen atom to which R is bonded and the carbonyl moiety to which R$_2$ is bonded;

each R$_3$ is independently linear or branched (C$_1$-C$_8$) alkyl residue, optionally substituted with one or more hydroxy, alkoxy or hydroxyalkoxy groups or combinations thereof, or taken together with R$_1$ and the nitrogen atom to which R$_3$ and R$_1$ are bonded, form a (C$_3$-C$_7$) cyclic residue, said cyclic residue being optionally interrupted by —O—, —S— or —NR$_4$—, and/or optionally substituted with one or more hydroxy, alkoxy or hydroxyalkoxy groups or combinations thereof;

each R$_4$ is independently hydrogen or a linear or branched (C$_1$-C$_8$) alkyl residue, optionally substituted with one or more hydroxy, alkoxy, hydroxyalkoxy groups or combinations thereof; and X is a bond or a linear or branched (C$_1$-C$_8$) alkylene chain which is optionally substituted by up to six hydroxy groups, said alkylene chain being optionally interrupted by —O—, —S—, —NR$_4$— or —N(R)C(O)— groups.

The present invention is further directed to mixtures comprising a monomer, a dimer, and at least one imaging agent other than the monomer and the dimer wherein the monomer corresponds to Formula I and the dimer corresponds to Formula II.

The present invention is further directed to a method of diagnostic imaging, the method comprising administering to an individual a contrast agent comprising a mixture of at least one monomer and at least one dimer, the monomer corresponding to Formula I and the dimer corresponding to Formula II, and carrying out an imaging procedure on such individual.

Other aspects and features of the present invention will be, in part, apparent, and, in part, pointed out hereinafter.

DETAILED DESCRIPTION OF THE PREFERRED EMBODIMENTS

In accordance with the present invention, it has been found that contrast media compositions corresponding to mixtures of at least one monomer of Formula I and at least one dimer of Formulae II, wherein the dimers of Formula II contain at least one primary carboxamide substituent and the monomers of Formula I do not contain any primary carboxamide substituents, have unexpectedly and favorably lower osmolality and viscosity values than would be predicted based solely upon the contribution of the monomer and dimer in the mixture. In a currently preferred embodiment, the contrast media composition corresponds to a mixture of a monomer of Formula I and a dimer of Formula II. Without being bound to any particular theory, in view of the nature of the differences in the substituents on the monomer and dimer it is surprising to find that compositions arising from such monomer-dimer mixtures have favorable intermolecular attractions between the dimers of Formula II and the monomers of Formula I that appear to result in molecular aggregation and thereby reduce the effective number of particles present in solution and hence, the osmolality of the mixture.

Advantageously, X-ray contrast media comprising a mixture of at least one monomer and at least one dimer of the present invention may be prepared with both improved viscosity and osmolality characteristics. Accordingly, mixtures of the present invention preferably comprise monomer and dimer in a weight ratio of iodine in the monomer and dimer, respectively, based on the iodine concentration in the mixture (e.g. in mg I/mL formulation). Broadly the weight ratio of iodine in the monomer to iodine in the dimer is about 1:20 to about 20:1. In one embodiment, the mixture comprises the monomer and dimer in a weight ratio of about 1:9 to about 9:1. In one preferred embodiment, for example, the mixture comprises the monomer and dimer in a weight ratio of about 1:5.7 to about 5.7:1. In another preferred embodiment, the mixture comprises the monomer and dimer in a weight ratio of about 1:9 to about 1:1. In yet another preferred embodiment, the mixture comprises the monomer and dimer in a weight ratio of about 1:3 to about 1:1.

As previously described, contrast media of the present invention comprise a monomer corresponding to Formula I.

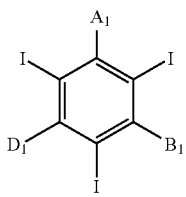

Formula (I)

wherein $A_1$, $B_1$ and $D_1$ are as previously defined. In one embodiment, $A_1$ and $B_1$ are each —C(O)N($R_3$)$R_1$ and $D_1$ is —N(R)C(O)$R_2$ with each $R_1$, $R_2$ and $R_3$ of $A_1$, $B_1$ and $D_1$, being independently selected from the range of substituents originally identified in connection with Formula I. For example, in this embodiment $A_1$ and $B_1$ may be —CONH$R_3$ wherein each $R_3$ of $A_1$ and $B_1$ is independently methyl, hydroxymethyl (—CH$_2$OH), ethyl, hydroxyethyl (—CH$_2$CH$_2$OH or —CH(OH)CH$_3$), propyl, hydroxypropyl (—CH$_2$CH$_2$CH$_2$OH) or dihydroxypropyl (—CH$_2$CH(OH)CH$_2$OH); more preferably, in this embodiment, each $R_3$ of $A_1$ and $B_1$ is independently hydroxyethyl (—CH$_2$CH$_2$OH or —CH(OH)CH$_3$), hydroxypropyl (—CH$_2$CH$_2$CH$_2$OH) or dihydroxypropyl (—CH$_2$CH(OH)CH$_2$OH). By way of further example, in this embodiment, the R and $R_2$ substituents of $D_1$ may independently be hydrogen, methyl, hydroxymethyl (—CH$_2$OH), ethyl, hydroxyethyl (—CH$_2$CH$_2$OH or —CH(OH)CH$_3$), propyl, hydroxypropyl (—CH$_2$CH$_2$CH$_2$OH), 2-methoxyethyl (—CH$_2$CH$_2$OCH$_3$), 1-methoxy-2-hydroxypropyl (—CH$_2$CH(OH)CH$_2$OCH$_3$), or dihydroxypropyl (—CH$_2$CH(OH)CH$_2$OH); more preferably, in this embodiment, the R and $R_2$ substituents of $D_1$ are preferably selected from methyl, hydroxymethyl (—CH$_2$OH), hydroxyethyl (—CH$_2$CH$_2$OH), 2-methoxyethyl (—CH$_2$CH$_2$OCH$_3$), and dihydroxypropyl (—CH$_2$CH(OH)CH$_2$OH). By way of further example, in this embodiment $A_1$ and $B_1$ may be —CON(CH$_3$)$R_3$ wherein each $R_3$ of $A_1$ and $B_1$ is independently methyl, hydroxymethyl (—CH$_2$OH), ethyl, hydroxyethyl (—CH$_2$CH$_2$OH or —CH(OH)CH$_3$), propyl, hydroxypropyl (—CH$_2$CH$_2$CH$_2$OH) or dihydroxypropyl (—CH$_2$CH(OH)CH$_2$OH); more preferably, in this embodiment, each $R_3$ of $A_1$ and $B_1$ is independently hydroxyethyl (—CH$_2$CH$_2$OH or —CH(OH)CH$_3$), hydroxypropyl (—CH$_2$CH$_2$CH$_2$OH) or dihydroxypropyl (—CH$_2$CH(OH)CH$_2$OH). By way of further example, in this embodiment, the R and $R_2$ substituents of $D_1$ may independently be, hydrogen, methyl, hydroxymethyl (—CH$_2$OH), ethyl, hydroxyethyl (—CH$_2$CH$_2$OH or —CH(OH)CH$_3$), propyl, hydroxypropyl (—CH$_2$CH$_2$CH$_2$OH), 2-methoxyethyl (—CH$_2$CH$_2$OCH$_3$), 1-methoxy-2-hydroxypropyl (—CH$_2$CH(OH)CH$_2$OCH$_3$), or dihydroxypropyl (—CH$_2$CH(OH)CH$_2$OH); more preferably, in this embodiment, the R and $R_2$ substituents of $D_1$ are preferably selected from methyl, hydroxymethyl (—CH$_2$OH), hydroxyethyl (—CH$_2$CH$_2$OH), 2-methoxyethyl (—CH$_2$CH$_2$OCH$_3$), and dihydroxypropyl (—CH$_2$CH(OH)CH$_2$OH).

In a preferred embodiment, the contrast media comprises a monomer selected from the group consisting of:

iomeprol {$C_{17}H_{22}I_3N_3O_8$; N,N'-bis(2,3-dihydroxypropyl)-5-[(hydroxyacetyl)methylamino]-2,4,6-triiodo-1,3-benzenedicarboxamide; CAS [RN] [78649-41-9]},

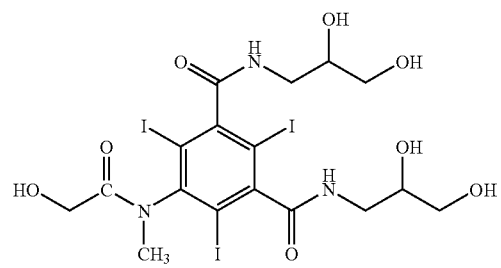

IOMEPROL iopromide {$C_{18}H_{24}I_3N_3O_8$; N,N'-bis(2,3-dihydroxypropyl)-2,4,6-triiodo-5-[(methoxyacetyl)amino]-N-methyl-1,3-benzenedicarboxamide; CAS [RN] [73334-07-3]},

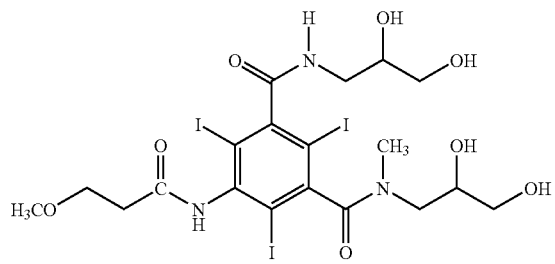

IOPROMIDE ioversol {$C_{18}H_{24}I_3N_3O_9$; N,N'-bis(2,3-dihydroxypropyl)-5-[(hydroxyacetyl)(2-hydroxyethyl)amino]-2,4,6-triiodo-1,3-benzenedicarboxamide; CAS [RN] [87771-40-2]},

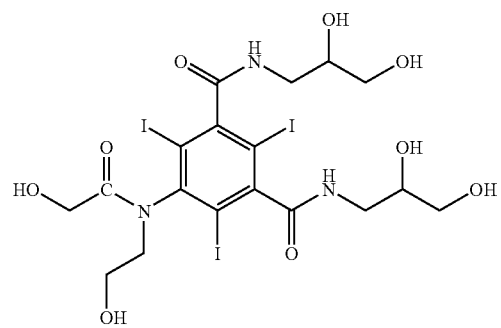

IOVERSOL iohexyl {$C_{19}H_{26}I_3N_3O_9$; 5-[acetyl(2,3-dihydroxypropyl)amino]-N,N'-bis(2,3-dihydroxypropyl)-2,4,6-triiodo-1,3-benzenedicarboxamide; CAS [RN] [66108-95-0]},

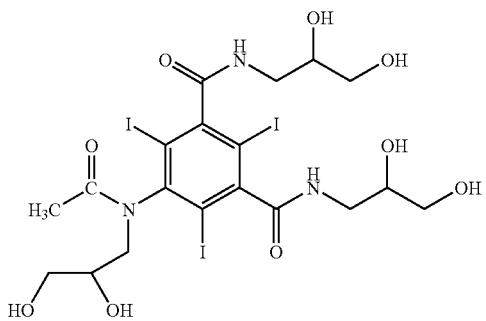

IOHEXOL

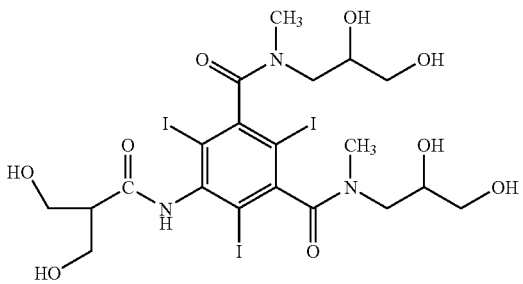

IOBITRIDOL iopentol {$C_{20}H_{28}I_3N_3O_9$; 5-[acetyl(2-hydroxy-3-methoxypropyl)amino]-N,N'-bis(2,3-dihydroxypropyl)-2,4,6-triiodo-1,3-benzenedicarboxamide, CAS [RN] [89797-00-2]},

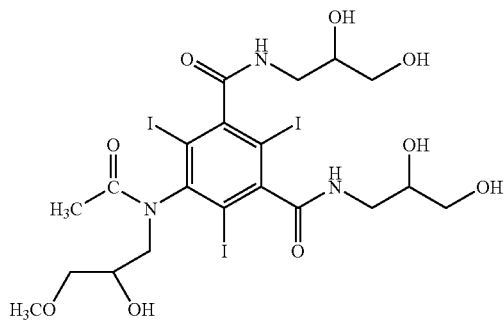

IOPENTOL iopamidol {$C_{17}H_{22}I_3N_3O_8$; 5-[(2-hydroxy-1-oxopropyl)amino]-N,N'-bis(2-hydroxy-1-(hydroxymethyl)ethyl)-2,4,6-triiodo-1,3-benzenedicarboxamide, CAS [RN] [60166-93-0]},

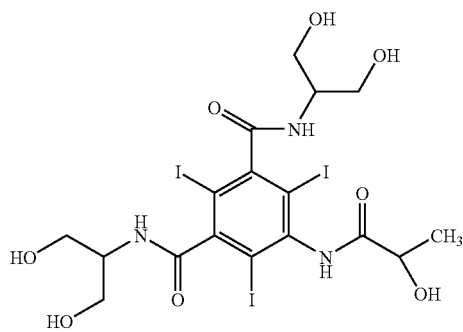

IOPAMIDOL and iobitridol {$C_{20}H_{28}I_3N_3O_9$; N N'-bis(2,3-dihydroxypropyl)-5-[[3-hydroxy-2-(hydroxymethyl)-1-oxopropyl]amino]-2,4,6-triiodo-N,N'-dimethyl-1,3-benzenedicarboxamide; CAS [RN] [136949-58-1]}

Contrast media of the present invention also contain a dimer corresponding to Formula II Formula (II)

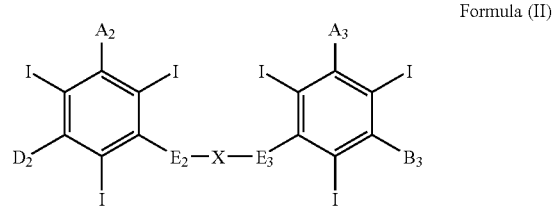

wherein $A_2$, $A_3$, $B_3$, $D_2$, $E_2$, $E_3$ and X are as previously defined. In one embodiment, X is methylene (—$CH_2$—) or ethylene (—$CH_2CH_2$—), preferably methylene, and $A_2$, $A_3$, $B_3$, $D_2$, $E_2$ and $E_3$ are as originally defined in connection with Formulae I and II. In another embodiment, each of $A_2$ and $A_3$ is —C(O)$NH_2$, each of $B_3$ and $D_2$ is —C(O)N(R)$R_1$, and $E_2$, $E_3$, and X and each R and $R_1$ are as originally defined in connection with Formulae I and II. In another embodiment, each of $A_2$ and $A_3$ is —C(O)$NH_2$, each of $B_3$ and $D_2$ is —CONHR, and $E_2$, $E_3$, and X and each R are as originally defined in connection with Formulae I and II. In another embodiment, each of $A_2$ and $A_3$ is —C(O)$NH_2$, each of $B_3$ and $D_2$ is —C(O)$NHR_1$, and -$E_2$-X-$E_3$- is —N(R)C(O)$CH_2$C(O)N(R)— and each R and $R_1$ is as originally defined in connection with Formulae I and II. In another embodiment, each of $A_2$ and $A_3$ is —C(O)$NH_2$, each of $B_3$ and $D_2$ is —CONHR, and -$E_2$-X-$E_3$- is —N(R)C(O)$CH_2$C(O)N(R)— and each R and $R_1$ is independently selected from hydrogen, methyl, hydroxymethyl (—$CH_2OH$), ethyl, hydroxyethyl (—$CH_2CH_2OH$ or —CH(OH)$CH_3$), propyl, hydroxypropyl (—$CH_2CH_2CH_2OH$) or dihydroxypropyl (—$CH_2CH(OH)CH_2OH$); more preferably, in this embodiment, each R and $R_1$ is independently hydroxyethyl, hydroxypropyl, or dihydroxypropyl. In yet another embodiment, the contrast media comprises iosmin (also known as iosimenol) {$C_{31}H_{36}I_6N_6O_{14}$; 5,5'-[(1,3-dioxo-1,3-propanediyl) bis [(2,3-dihydroxypropyl) imino]]bis[N-(2,3-dihydroxypropyl)-2,4,6-triiodo-1,3-benzenedicarboxamide; CAS [RN] [181872-90-2]} as the dimer:

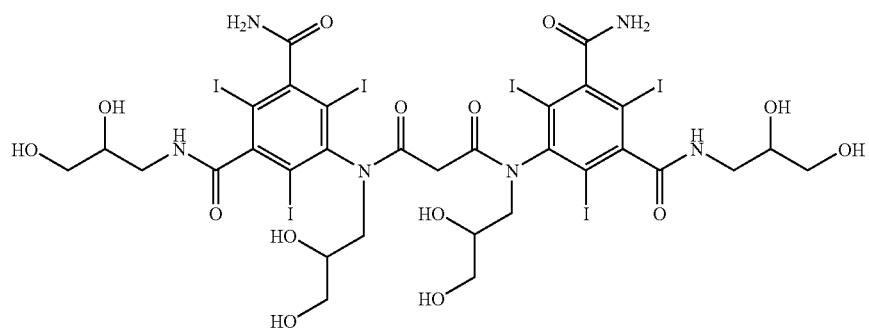

IOSMIN

In a preferred embodiment, the contrast media comprises the dimer of Formula II, preferably iosmin, together with one or more monomers selected from the group consisting of iomeprol, ioversol, iohexyl, iopamidol, iopromide, iobitridol and iopentol, preferably ioversol, iohexyl, and iopamidol, and more preferably ioversol.

Optionally, the contrast media of the present invention further comprises an imaging agent of a class not corresponding to either of Formulae I and II. For example, the contrast media may additionally comprise X-ray contrast imaging agents not corresponding to Formula I or II. Alternatively, the contrast media may comprise other types of imaging agents such as ultrasound, magnetic resonance (MR), radionuclide, and optical imaging agents and may be used for other imaging applications. Other types of imaging agents are described in H. S Thomsen, R. N. Muller and R. F. Mattrey, Editors, Trends in Contrast Media, (Berlin: Springer-Verlag, 1999); and E. M. Sevick-Muraca, et al., Near-Infrared Imaging with Fluorescent Contrast Agents, In: M.-A. Mycek and B. W. Pogue, Editors, Handbook of Biomedical Fluorescence, (New York: Marcel-Dekker, 2003, chapter 14); and Textbook of Contrast Media Edited by Peter Dawson, David Cosgrove and Ronald Grainger, ISIS Medical Media 1999; and are hereby incorporated by reference. Broadly, the amount of such optional imaging agent is about 0.01 to about 15 mole percent based on the total moles of monomer and dimer in the mixture.

Radiological compositions may be prepared containing the above mentioned mixtures of iodinated nonionic compounds as an x-ray contrast agent together with a pharmaceutically acceptable radiological vehicle by following established methods used to manufacture such injectable formulations. Pharmaceutically acceptable radiological vehicles include those that are suitable for injection such as aqueous buffer solutions; e.g., tris(hydroxymethyl)amino methane (and its salts), phosphate, citrate, bicarbonate, etc., sterile water for injection, physiological saline, and balanced ionic solutions containing chloride and/or bicarbonate salts of normal blood plasma cations such as Ca, Na, K and Mg, and other halides, carbonates, sulphates, phosphates of Na, K, Mg, Ca. Other buffer solutions are described in Remington's Practice of Pharmacy, Eleventh Edition, for example on page 170. The vehicles may advantageously contain a small amount (e.g., from about 0.01 to about 15.0 mole %) of a chelating agent such as ethylenediamine tetraacetic acid (EDTA), calcium disodium EDTA, or other pharmaceutically acceptable chelating agents such as calcium monosodium DTPA-BMEA (Versetamide; Mallinckrodt Inc.). The composition further comprises non-radiographic additives selected from the group consisting of excipients, such as, for example, glycerol, polyethylene glycol or dextran, and anticlotting agents, such as, for example, heparin or hirudin.

The concentration of the x-ray contrast agent of the present invention in the pharmaceutically acceptable vehicle, e.g., water, will vary with the particular field of use. A sufficient amount is present to provide satisfactory x-ray visualization. For example, when using aqueous solutions for angiography, the concentration of iodine is broadly about 100 to about 500 mg/ml, preferably about 140 to about 400 mg/ml, and the dose is in the range of 25-300 ml. The radiological composition is administered so that the contrast agent remains in the living animal body for about 0.5 to 3 hours, although shorter or longer residence periods are acceptable as needed. Thus, for vascular visualization, the mixture disclosed herein and analogous mixtures may be formulated conveniently in vials, bottles, ampules or prefilled syringes containing 10 to 2000 ml of an aqueous solution. These containers may be made of glass, plastic or other materials suitable for pharmaceutical products.

In one embodiment, the mixtures of this invention may be formulated as micelles, liposomes and micro/nano particles. These formulations may enhance delivery and localization of the inventive compositions to/at the desired organ or site. The target specificity of these formulations can be enhanced by incorporating suitable targeting molecules such as peptides, saccharides, fatty acids, and the like. Preparation and uses of these formulations are well known in the art.

The diagnostic compositions of the invention are used in the conventional manner. The compositions may be administered to a patient, typically a warm-blooded animal, either systemically or locally to the organ or tissue to be imaged, optimally using a power injector when appropriate, and the patient then subjected to the imaging procedure. For example, in the case of selective coronary arteriography, an amount of the radiological composition, sufficient to provide adequate visualization, is injected into the coronary system and the system is scanned with a suitable device such as a fluoroscope. The agent may be used in various other radiographic procedures e.g., in cardiography, coronary arteriography, aortography, cerebral and peripheral angiography, orthography, intravenous pyelography and urography.

X-ray contrast Imaging Procedures are found in Albert A. Moss, M. D., Gordon Gamsu, M. D., and Harry K. Genant, M. D., Computed Tomography of the Body, (Philadelphia, Pa.: W.B. Saunders Company, 1992) and M. Sovak, Editor, Radio-contrast Agents, (Berlin: Springer-Verlag, 1984).

The following examples illustrate the invention and are not limiting. In each of the examples, osmolality is determined at 37° C. using the Wescor 5500 Vapor Pressure Osmometer. Viscosity is determined at 25° C. and 37° C. using Brookfield Analog Micro Viscometer Model LVT or Digital Model DV-II+ Cone/Plate Viscometer.

Example 1

1A. 320 mgI/ml Iosimenol Injection formulation: 62.13 grams of Iosimenol, 0.224 grams of Tromethamine, 0.1 grams of Edetate calcium disodium and 0.22 grams of NaCl were mixed in 75 ml of water for injection (WFI) at room temperature (RT) until completely dissolved. The pH was adjusted to ~6.8 using 1N hydrochloric acid solution or 1N sodium hydroxide solution and the formulation was brought up to the final volume of 100 ml with WFI. A 50 ml aliquot of the above formulation in a bottle was autoclaved at 121° C. for 20 minutes. Both autoclaved and unautoclaved above samples were tested for osmolality (at 37° C.) and viscosity (at 25° C. and 37° C.) values using established methods.

1B. Mixed XRCM Formulation: Equal amounts (on a volume basis) of above unautoclaved Iosimenol Injection formulation and 320 mgI/ml of the commercial formulation of Ioversol (OPTIRAY-320; sold by Mallinckrodt Inc., St. Louis Mo., USA) were mixed. One milliliter of OPTIRAY-320 contains 678 mg of ioversol with 3.6 mg of tromethamine as a buffer, 0.2 mg of edetate calcium disodium as a stabilizer with pH adjusted between 6 and 7.4 with hydrochloric acid or sodium hydroxide. A portion of this mixed formulation was autoclaved at 121° C. for 20 minutes.

Autoclaved and unautoclaved samples were tested for osmolality (at 37° C.) and viscosity (at 25° C. and 37° C.) values using established methods and the values are tabulated (Table 1). Table 1 summarizes the osmolality and viscosity of the Iosimenol for Injection, Experiment 1A, before and after autoclave (Nos. 1 and 2 respectively), and of the mixed MRCM formulation, Experiment 1B, before and after autoclave (Nos. 3 and 4 respectively). The osmolality and viscosity values for the autoclaved and unautoclaved samples are comparable. Therefore, subsequent samples were not autoclaved.

TABLE 1

Mixed XRCM Formulation-320 mgI/ml

| No. | Ioversol 320 mgI/ml | Iosimenol Injection | Auto-claved | Osmolality (mOsm/kg) 37° C. | Viscosity (cps) 25° C. | Viscosity (cps) 37° C. |
|---|---|---|---|---|---|---|
| 1. | 0% | 100% | No | 286 | 15.5 | 8.9 |
| 2. | 0% | 100% | Yes | 288 | 15.2 | 8.7 |
| 3. | 50% | 50% | No | 485 | 10.1 | 6.3 |
| 4. | 50% | 50% | Yes | 486 | 10.2 | 6.2 |

Example 2

A 320 mgI/ml Iosimenol formulation was prepared following the procedure defined in Example 1A, except no NaCl was added. The formulation was not autoclaved.

An Ioversol 320 mgI/ml formulation (OPTIRAY-320) was mixed with the above Iosimenol formulation in different ratios. Osmolality (at 37° C.) and viscosity (at 25° C. and 37° C.) were measured for the starting samples and the unautoclaved, mixed samples following established methods. The results are summarized in Table 2. For sample set Nos. 1, 3 and 4, the individual (Iosimenol and Ioversol) and the mixed samples were tested on the same day. For sample set No. 2, the individual samples and the mixed sample were also tested on the same day but on a day other than the testing day for sample set Nos. 1, 3 and 4. Table 2 also lists the theoretically expected values of osmolality and viscosity for the mixtures (Theory). These theoretical values were calculated based on the percentage contributions from the pure samples.

TABLE 2

Mixed XRCM Formulation-320 mgI/ml

| No. | Ioversol 320 mgI/ml | Iosimenol Without NaCl | | Osmolality (mOsm/kg) 37° C. | Viscosity (cps) 25° C. | Viscosity (cps) 37° C. |
|---|---|---|---|---|---|---|
| 1. | 100% | 0% | | 680 | 9.2 | 6.0 |
|  | 0% | 100% | | 201 | 11.5 | 6.8 |
|  | 30% | 70% | | 338 | 10.0 | 6.2 |
|  |  |  | Theory | 345 | 10.8 | 6.56 |
| 2. | 100% | 0% | | 702 | 9.2 | 5.7 |
|  | 0% | 100% | | 194 | 11.8 | 6.5 |
|  | 50% | 50% | | 430 | 9.6 | 5.8 |
|  |  |  | Theory | 448 | 10.5 | 6.1 |
| 3. | 100% | 0% | | 680 | 9.2 | 6.0 |
|  | 0% | 100% | | 201 | 11.5 | 6.8 |
|  | 70% | 30% | | 534 | 9.3 | 6.0 |
|  |  |  | Theory | 536 | 9.9 | 6.24 |
| 4. | 100% | 0% | | 680 | 9.2 | 6.0 |
|  | 0% | 100% | | 201 | 11.5 | 6.8 |
|  | 90% | 10% | | 640 | 9.3 | 5.9 |
|  |  |  | Theory | 632 | 9.43 | 6.08 |

Example 3

The autoclaved Iosimenol Injection formulation (IF) sample from Example 1A was diluted to a concentration of 300 mgI/ml with WFI. Commercial 300 mgI/ml samples of Ioversol (OPTIRAY-300, sold by Mallinckrodt Inc, St. Louis Mo., USA), of Iopamidol (ISOVUE-300 sold by Bracco, Milan, ITALY) and of Iohexol (OMNIPAQUE-300 sold by Amersham, London, UK) were obtained.

Each milliliter of OPTIRAY-300 contains 636 mg of ioversol with 3.6 mg of tromethamine as a buffer, 0.2 mg of edetate calcium disodium as a stabilizer and the pH was adjusted between 6 and 7.4 with hydrochloric acid or sodium hydroxide. Each milliliter of ISOVUE-300 contains 612 mg of iopamidol with 1 mg tromethamine as a buffer, 0.39 mg edetate calcium disodium as a stabilizer and the pH adjusted between 6.5 and 7.5 with hydrochloric acid or sodium hydroxide. Each milliliter of OMNIPAQUE-300 contains 647 mg of iohexyl, 1.21 mg tromethamine, 0.1 mg edetate calcium disodium and the pH adjusted between 6.8 and 7.7 with hydrochloric acid or sodium hydroxide.

Iosimenol Injection (300 mgI/ml) formulation (IF) was mixed with individual 300 mgI/ml commercial formulations of Ioversol (OPTIRAY-300), Iopamidol (ISOVUE-300) and Iohexyl (OMNIPAQUE-300) in equal amounts (on a volume basis). Osmolality (at 37° C.) and viscosity (at 25° C. and 37° C.) values were measured for all samples (N=7) following established methods. The results are summarized in Table 3. Values for "Theory" are as described for Example 2.

TABLE 3

Mixed XRCM Formulation-300 mgI/ml

| No. | Composition | Osmolality, (mOsm/kg) 37° C. | Viscosity (cps) 25° C. | Viscosity (cps) 37° C. |
|---|---|---|---|---|
| 1. | Iosimenol Injection (IF) | 273 | 10.9 | 6.3 |
|  | Ioversol | 657 | 7.6 | 4.8 |
|  | 50% IF + 50% Ioversol | 444 | 8.2 | 5.2 |
|  | Theory | 465 | 9.25 | 5.55 |
| 2. | Iosimenol Injection (IF) | 273 | 10.9 | 6.3 |
|  | Iopamidol | 654 | 7.1 | 4.6 |
|  | 50% IF + 50% Iopamidol | 463 | 7.9 | 5.0 |
|  | Theory | 463 | 9.0 | 5.45 |
| 3. | Iosimenol Injection (IF) | 273 | 10.9 | 6.3 |
|  | Iohexol | 691 | 9.5 | 5.9 |
|  | 50% IF + 50% Iohexol | 478 | 9.1 | 5.7 |
|  | Theory | 482 | 10.2 | 6.1 |

Example 4

A 320 mgI/ml Iosimenol Injection formulation was made as described in Example 1A. To 10 ml of the Iosimenol formulation was mixed with 1.059 grams of Ioversol powder to give 370 mgI/ml of mixed formulation (13.5% iodine from monomer/86.5% iodine from dimer). The osmolality at 37° C. was determined to be 277 mOsm/kg. The viscosity value at 37° C. was determined to be 9.1 centipoise (cps).

What is claimed is:

1. An injectable radiological composition for x-ray visualization during radiological examinations, the composition comprising a pharmaceutically acceptable vehicle and a mixture of at least one monomer and at least one dimer, the monomer corresponding to Formula I and the dimer corresponding to Formula II

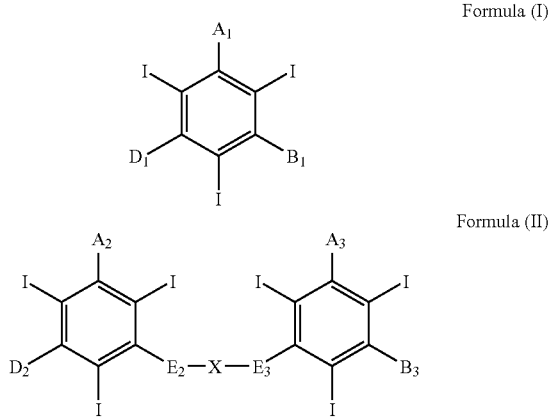

Formula (I)

Formula (II)

wherein, with regard to Formula I:
A$_1$ and B$_1$ are —CON(R$_3$)R$_1$;
D$_1$ is —N(R)C(O)R$_2$;
  each R and R$_2$ is independently H, or a linear or branched (C$_1$-C$_8$) alkyl residue, optionally substituted by one or more hydroxy, alkoxy or hydroxyalkoxy groups or combinations thereof;
  each R$_1$ is independently (i) hydrogen, or (ii) a linear or branched (C$_1$-C$_8$) alkyl residue, optionally substituted with one or more hydroxy, alkoxy, hydroxyalkoxy groups or combinations thereof;
  each R$_3$ is independently linear or branched (C$_1$-C$_8$) alkyl residue, optionally substituted with one or more hydroxy, alkoxy or hydroxyalkoxy groups or combinations thereof;
and wherein with regard to Formula II:
A$_2$ and A$_3$ are —CONH$_2$;
B$_3$ and D$_2$ are —CON(R)R$_1$;
E$_2$ and E$_3$ are independently selected from the group consisting of —CON(R)—, —N(R)C(O)— and —N(COR$_2$)—;
each R is independently H, or a linear or branched (C$_1$-C$_8$) alkyl residue, optionally substituted by one or more hydroxyl, alkoxy or hydroxyalkoxy groups or combinations thereof;
each R$_1$ is independently (i) hydrogen, (ii) a linear or branched (C$_1$-C$_8$) alkyl residue, optionally substituted by one or more hydroxyl, alkoxy or hydroxyalkoxy groups or combinations thereof, or (iii) the residue of a carbohydrate;
or R and R$_1$ are each members of a (C$_3$-C$_7$) cyclic residue further comprising the nitrogen atom to which each of R and R$_1$ is bonded, said cyclic residue being optionally interrupted by —O—, —S— or —NR$_4$—, and/or optionally substituted by one or more hydroxy, alkoxy or hydroxyalkoxy groups or combinations thereof;
each R$_2$ is independently a linear or branched (C$_1$-C$_8$) alkyl residue, optionally substituted by one or more hydroxyl, alkoxy or hydroxyalkoxy groups or combinations thereof;
each R$_4$ is independently hydrogen or a linear or branched (C$_1$-C$_8$) alkyl residue, optionally substituted by one or more hydroxyl, alkoxy or hydroxyalkoxy groups or combinations thereof; and
X is a bond or a linear or branched (C$_1$-C$_8$) alkylene chain which is optionally substituted by up to six hydroxyl groups, said alkylene chain being optionally interrupted by —O—, —S—, —NR$_4$— or —N(R)C(O)— groups.

2. The composition of claim 1 wherein with regard to Formula I, R$_1$ is H or methyl.

3. The composition of claim 1 wherein X is methylene.

4. The composition of claim 1 wherein with regard to Formula I:
A$_1$ and B$_1$ are —CON(R$_3$)R$_1$;
D$_1$ is —N(R)C(O)R$_2$;
each R and R$_2$ is independently H, methyl, hydroxymethyl, ethyl, hydroxyethyl, propyl, hydroxypropyl, 2-methoxyethyl, 1-methoxy-2-hydroxypropyl or dihydroxypropyl;
each R$_1$ is independently H or methyl;
each R$_3$ is independently methyl, hydroxymethyl, ethyl, hydroxyethyl, propyl, hydroxypropyl or dihydroxypropyl;
and wherein with regard to Formula II:
A$_2$ and A$_3$ are —CONH$_2$;
B$_3$ and D$_2$ are —CON(R)R$_1$;
E$_2$ and E$_3$ are independently selected from the group consisting of —CON(R)—, —N(R)C(O)— and —N(COR$_2$)—;
each R is independently H, or a linear or branched (C$_1$-C$_8$) alkyl residue, optionally substituted by one or more hydroxyl, alkoxy or hydroxyalkoxy groups or combinations thereof;
each R$_1$ is independently (i) hydrogen, (ii) a linear or branched (C$_1$-C$_8$) alkyl residue, optionally substituted by one or more hydroxyl, alkoxy or hydroxyalkoxy groups or combinations thereof, or (iii) the residue of a carbohydrate;

or R and R$_1$ are each members of a (C$_3$-C$_7$) cyclic residue further comprising the nitrogen atom to which each of R and R$_1$ is bonded, said cyclic residue being optionally interrupted by —O—, —S— or —NR$_4$—, and/or optionally substituted by one or more hydroxy, alkoxy or hydroxyalkoxy groups or combinations thereof;

each R$_2$ is independently a linear or branched (C$_1$-C$_8$) alkyl residue, optionally substituted by one or more hydroxyl, alkoxy or hydroxyalkoxy groups or combinations thereof;

each R$_4$ is independently hydrogen or a linear or branched (C$_1$-C$_8$) alkyl residue, optionally substituted by one or more hydroxyl, alkoxy or hydroxyalkoxy groups or combinations thereof; and X is a bond or a linear or branched (C$_1$-C$_8$) alkylene chain which is optionally substituted by up to six hydroxyl groups, said alkylene chain being optionally interrupted by —O—, —S—, —NR$_4$— or —N(R)C(O)— groups.

5. The composition of claim 1 wherein A$_1$ and B$_1$ are —CONHR$_3$.

6. The composition of claim 1 wherein each R$_1$ and R$_3$ of A$_1$ and B$_1$ is independently methyl, hydroxymethyl, ethyl, hydroxyethyl, propyl, hydroxypropyl, or dihydroxypropyl.

7. The composition of claim 1 wherein the R and R$_2$ substituents of D$_1$ are independently methyl, hydroxymethyl, ethyl, hydroxyethyl, propyl, hydroxypropyl, 1-methoxy-2-hydroxypropyl, or dihydroxypropyl.

8. The composition of claim 7 wherein A$_1$ and B$_1$ are —CONHR$_3$.

9. The composition of claim 7 wherein each R$_1$ and R$_3$ of A$_1$ and B$_1$ is independently methyl, hydroxymethyl, ethyl, hydroxyethyl, propyl, hydroxypropyl, or dihydroxypropyl.

10. The composition of claim 1 wherein R$_1$ is hydrogen.

11. The composition of claim 1 wherein B$_3$ and D$_2$ are —CONHR.

12. The composition of claim 1 wherein the monomer is selected from the group consisting of iomeprol, iopromide, ioversol, iohexol, iopentol, iopamidol and iobitridol.

13. The composition of claim 1 wherein the dimer is iosmin.

14. The composition of claim 1 wherein the monomer is selected from the group consisting of ioversol, iohexol, and iopamidol, and the dimer is iosmin.

15. The composition of claim 1 wherein the monomer is ioversol and the dimer is iosmin.

16. The composition of claim 1 wherein the composition further comprises pharmaceutically acceptable radiological vehicles selected from the group consisting of aqueous buffer solutions, sterile water for injection, physiologic saline, balanced ionic solutions, a chelating agent, and other non-radioactive additives comprising excipients and anticlotting agents.

17. The composition of claim 16 wherein said aqueous buffer solutions comprise tris(hydroxyethyl)amino methane and salts thereof, phosphate, citrate and bicarbonates; wherein said balanced ionic solutions comprise chlorides and bicarbonates of cations selected from the group consisting of Ca, Na, K, and Mg, and other halides, carbonates, sulphates, phosphates of Na, K, Mg and Ca; wherein said chelating agents consist of H$_4$EDTA, EDTACaNa$_2$ and calcium monosodium DTPA-BMEA; wherein said excipient is glycerol, polyethylene glycol or dextran; and wherein said anticlotting agent is heparin or hirudin.

18. A method of diagnostic imaging, the method comprising administering to an individual a composition of claim 1, and carrying out an imaging procedure on such individual.

19. The method of claim 18 wherein said composition comprises a monomer selected from the group consisting of ioversol, iohexol and iopamidol, and the dimer is iosimenol.

20. The method of claim 18 wherein said composition comprises a mixture of ioversol, and iosimenol.

21. A composition for use in a diagnostic imaging procedure, the composition comprising:
iosimenol; and,
at least one monomer selected from the group consisting of ioversol, iohexol, and iopamidol.

22. The composition of claim 21, wherein the at least one monomer comprises ioversol.

23. The composition of claim 21, wherein the at least one monomer comprises iohexol.

24. The composition of claim 21, wherein the at least one monomer comprises iopamidol.

25. The composition of claim 21, further comprising a pharmaceutically acceptable vehicle.

26. The composition of claim 25, wherein the pharmaceutically acceptable vehicle is selected from the group consisting of aqueous buffer solutions, sterile water for injection, physiologic saline, balanced ionic solutions, a chelating agent, and other non-radioactive additives comprising excipients and anticlotting agents.

27. The composition of claim 26, wherein:
said aqueous buffer solutions are selected from the group consisting of tris(hydroxyethyl)amino methane and salts thereof, phosphate, citrate and bicarbonates;
said balanced ionic solutions are selected from the group consisting of chlorides and bicarbonates of cations selected from the group consisting of Ca, Na, K, and Mg, and other halides, carbonates, sulphates, phosphates of Na, K, Mg and Ca;
said chelating agents selected from the group consisting of H$_4$EDTA, EDTACaNa$_2$ and calcium monosodium DTPA-BMEA;
said excipients are selected from the group consisting of glycerol, polyethylene glycol and dextran; and,
wherein said anticlotting agent is selected from the group consisting of heparin and hirudin.

28. The composition of claim 21, further comprising an additional contrast agent different than the at least one monomer and the iosimenol.

29. The composition of claim 28, wherein said additional contrast agent is selected from the group consisting of X-ray contrast agents, magnetic resonance imaging agents, radionuclide imaging agents, ultrasound imaging agents, and optical imaging agents.

* * * * *